United States Patent
Ewing et al.

[11] Patent Number: 5,928,479
[45] Date of Patent: *Jul. 27, 1999

[54] PROCESS FOR THE PURIFICATION OF PENTAFLUOROETHANE

[75] Inventors: Paul Nicholas Ewing, Stockton Heath; Stuart Corr, Appleton; John Stuart Martin, Hartford; Michael John Watson, Long Newton, all of United Kingdom

[73] Assignee: Imperial Chemical Industries PLC, United Kingdom

[*] Notice: Under 35 U.S.C. 154(b), the term of this patent shall be extended for 423 days.

[21] Appl. No.: 08/716,370
[22] PCT Filed: Mar. 27, 1995
[86] PCT No.: PCT/GB95/00672
§ 371 Date: Sep. 19, 1996
§ 102(e) Date: Sep. 19, 1996
[87] PCT Pub. No.: WO95/27689
PCT Pub. Date: Oct. 19, 1995

[30] Foreign Application Priority Data

Apr. 8, 1994 [GB] United Kingdom ............... 9406961
Sep. 6, 1994 [GB] United Kingdom ............... 9417868
Oct. 11, 1994 [GB] United Kingdom ............... 9420510

[51] Int. Cl.[6] ........................................ B01D 3/34
[52] U.S. Cl. .................. 203/67; 203/99; 570/178; 570/179
[58] Field of Search ............ 203/67, 99; 570/178, 570/179

[56] References Cited

U.S. PATENT DOCUMENTS

| | | | |
|---|---|---|---|
| 3,732,150 | 5/1973 | Bailey | 203/44 |
| 4,843,181 | 6/1989 | Gumprecht et al. | 570/169 |
| 5,346,595 | 9/1994 | Clemmer et al. | 203/75 |
| 5,367,103 | 11/1994 | Guglielmo et al. | 570/177 |
| 5,421,964 | 6/1995 | Mahler et al. | 203/51 |
| 5,453,551 | 9/1995 | Lacroix et al. | 570/177 |
| 5,585,529 | 12/1996 | Corbin et al. | 570/179 |

FOREIGN PATENT DOCUMENTS

WO 92/20640 11/1992 WIPO.

Primary Examiner—Nina Bhat

[57] ABSTRACT

A process for the purification of pentafluoroethane by removing chloropentafluoroethane therefrom which comprises adding to the impure pentafluoroethane a component which undergoes a non-ideal interaction with chloropentafluoroethane and/or with the azeotrope of chloropentafluoroethane and pentafluoroethane such that the volatility of chloropentafluoroethane and/or the azeotrope of chloropentafluoroethane and pentafluoroethane relative to bulk pentafluoroethane is increased and distilling the mixture.

23 Claims, 1 Drawing Sheet

PROCESS FOR THE PURIFICATION OF PENTAFLUOROETHANE

This invention relates to a process for the purification of pentafluoroethane (HFA 125) and particularly to a process for removing the impurity chloropentafluoroethane (CFC 115) from pentafluoroethane.

Recently, processes have been proposed for the production of pentafluoroethane which has been proposed, together with other hydrofluoroalkanes such as 1,1,1,2-tetrafluoroethane, difluoromethane and 1,1,1-trifluoroethane, and blends thereof, as a suitable replacement for chlorofluorocarbons and hydrochlorofluorocarbons due to the zero ozone depleting potential of hydrofluoroalkanes.

Thus it has been proposed in Japanese Patent Application Nos Kokai 3099026, 1258632 and 4029941 to produce pentafluoroethane by contacting pentafluorochloroethane with hydrogen in the presence of a hydrogenation catalyst. Suitable conditions of temperature and pressure and suitable catalysts are described in the aforementioned Japanese patent applications.

It has also been proposed to manufacture HFA 125 by the fluorination of perchloroethylene, chlorotetrafluoroethane and/or dichlorotrifluoroethane by reacting perchloroethylene, chlorotetrafluoroethane and/or dichlorotrifluoroethane with hydrogen fluoride in the vapour phase at a temperature in the range of about 200° C. to 500° in the presence of a fluorination catalyst such as alumina, aluminium fluoride, aluminium oxyfluoride, chromia, halogenated chromia or chromium oxyhalide. The fluorination catalyst may also comprise one or more metals other than chromium or aluminium, for example zinc and/or nickel in combination with alumina and/or chromia.

However, these and other processes for the production of pentafluoroethane result in a product comprising pentafluoroethane together with impurities, in particular the chlorofluorocarbon impurity chloropentafluoroethane (CFC 115).

The removal of CFC 115 from HFA 125 by distillation is possible in theory but is impractical; the boiling points of the components are −38.7° C. and −48° C. respectively at atmospheric pressure and of the azeotrope thereof is −55° C. at atmospheric pressure. To obtain pure 125 requires large stills with very low condenser temperatures. Moreover, the azeotropic composition is rich in 125 (around 90 wt % HFA 125) and hence azeotropic distillation is wasteful of HFA 125. The separation is even more difficult at superatmospheric pressure, where the relative volatility of HFA 125 versus CFC 115 is close to 1.0 as HFA 125 purity of 100% is approached.

We have now found that CFC 115 can be effectively removed from HFA 125 by a technique herein termed third component distillation.

According to the present invention there is provided a process for the purification of pentafluoroethane by removing chloropentafluoroethane therefrom which comprises adding to the impure pentafluoroethane a component which undergoes a non-ideal interaction with chloropentafluoroethane and/or with the azeotrope of chloropentafluoroethane and pentafluoroethane such that the volatility of chloropentafluoroethane and/or the azeotrope of chloropentafluoroethane and pentafluoroethane relative to bulk pentafluoroethane is increased and distilling the mixture.

The component added to the impure HFA 125 to increase the relative volatility of the CFC 115 is referred to hereinafter for convenience as "the third component" although it is to be understood that the invention is not limited to treatment of compositions containing only the two components HFA 125 and CFC 115.

The third component may be any compound which undergoes a non-ideal interaction with CFC 115 and/or the azeotrope of CFC 115 and HFA 125 whereby to increase the volatility of the CFC 115 relative to bulk HFA 125 and thereby enable removal of the CFC 115 from the HFA 125 by simple distillation. In general, the compound preferably will be polar and will have a boiling point below that of HFA 125 so that its effect is to increase the volatility of CFC 115 relative to bulk HFA 125 thereby enabling its removal as a top product from a distillation column or still whilst the HFA 125 is collected as a bottoms product from the column or still. Typically, in this case, the third component will have a boiling point less than −50° C. We especially prefer to employ a third component having a boiling point in the range of about −50° C. to −100° C. at atmospheric pressure.

A wide variety of compounds may be employed as the third component which may be an organic or inorganic compound. Examples of suitable inorganic compounds include hydrogen chloride (as well as mixtures thereof, for example with hydrogen fluoride) and carbon dioxide. Where an organic compound is employed, the organic compound may contain one or more carbon atoms. Where it contains two or more carbon atoms, the compound may be ethylenically unsaturated or saturated. Mixtures of third components may be employed, if desired. The identification and selection of the third component is a matter of simple routine experiment on a trial and error basis. We prefer that the third component is selected from the group consisting of hydrogen chloride, carbon dioxide or a compound of formula $CF_2HX$ where X is Cl or H. We especially prefer to employ difluoromethane (HFC 32) as the third component.

A factor which may affect the selection of the optimum third component is the subsequent treatment of the interaction product containing CFC 115 which is removed from the distillation column or still; if this interaction product is disposed of by destruction, for example by thermal oxidation, then the amount of the third component not readily separable from CFC 115 should be minimised.

The selection of the optimum third component is often a compromise between high efficiency of CFC 115 removal, undesirable interaction with HFA 125 and subsequent separation and/or disposal of the CFC 115/third component interaction product. We have found, though, that a particularly useful third component is difluoromethane.

The amount of third component added to the mixture will depend to a large extent upon the particular compound employed and the amount of the CFC 115 to be removed from the HFA 125. In general, however, and as a guide, the amount by weight ratio of the third component to CFC 115 in the mixture to be treated will be in the range from 1:2 to 200:1. More particularly where the third component is a compound of formula $CF_2HX$ where X is Cl or H, the weight ratio will be in the range from 1:2 to 10: 1and the amount by weight of the third component will usually be about equal to the amount by weight of CFC 115 to be removed. Where the third component is hydrogen chloride, the weight ratio is preferably in the range from 50:1 to 200:1.

The third component may be generated in situ. Thus, where the 115/125 mixture is produced by hydrogenation of 115, a compound may be co-fed to the hydrogenation process which, under the hydrogenation conditions is converted to the third component, or where the 115/125 mixture is produced by hydrofluorination, then a compound may be co-fed to the hydrofluorination reaction which the under the hydrofluorination conditions is converted to the third component. Thus for example, where the third component is difluoromethane, 12/22 may be fed to the hydrogenation reaction together with 115 and methylene chloride may be feed to the hydrofluorination reaction. Alternatively, where the third component employed is hydrogen chloride, the hydrogen chloride may be generated as a by-product of the HFA 125 production process, for example the hydrofluorination of perchloroethylene/dichlorotrifluoroethane and the hydrogenation of chloropentafluoroethane.

Distillation of the mixture may be carried out at atmospheric, superatmospheric or subatmospheric pressure, superatmospheric pressure of from about 2 bar to about 15 bar, especially from about 2 bar to about 10 bar, being preferred. The temperature profile within the distillation column or still will usually be such that distillation occurs under conditions of partial reflux, for example a bottoms (HFA 125) fraction temperature of about 10° C. to 30° C. at about 10 bar pressure.

The process is useful for the treatment of HFA 125 containing a wide range of amounts of CFC 115 impurity, for example as little as 0.1% CFC 115 or as much as 20% (or even more) CFC 115. Where the amount of the impurity is low a single pass through the distillation column or still will usually be sufficient to reduce the impurity level in the HFA 125 to an acceptable level, eg below 10 ppm, whilst where the initial impurity level is high it may be desirable to pass the HFA 125 through the column or still more than once to employ more than one column or still to excessively reduce the level of the impurity.

The products of the separation are a bottoms fraction comprising purified HFA 125 and an overheads fraction comprising CFC 115 and the third component. The overheads fraction may be disposed of, for instance by thermal oxidation, but if desired it may be separated, for example by further reaction of the CFC 115 content eg by hydrogenation or reaction with $LiAlH_4$. The third component thus obtained may be recycled to the HFA 125 purification stage.

It is possible, by careful control of the operating conditions, to obtain a bottoms fraction (HFA 125) essentially free from CFC 115 and an overheads fraction essentially free from HFA 125 in a single separation stage. However it may be preferable in practice to effect the separation in two stages. In one embodiment of the two stage process, the overheads fraction from the first stage contains some HFA 125 and comprises the third component, CFC 115 and HFA 125 and the bottoms fraction comprises HFA 125. The overheads fraction is then separated in a second stage to obtain a second-stage overheads fraction comprising the third component and CFC 115 and a second-stage bottoms fraction comprising the third component and HFA 125. Where the third component is difluoromethane, the second-stage bottoms fraction may be collected for use as or as a component of refrigerant compositions (blends) or it may be recycled to the first-stage separation column or still.

In another embodiment of the two stage process the overheads fraction from the first stage comprises the third component, CFC 115 and possibly a small amount of HFA 125 and the bottoms fraction comprises the third component and BFA 125. The first-stage bottoms fraction is passed together with additional third component to a second stage column or still from which are withdrawn a second-stage bottoms fraction comprising essentially pure HFA 125 and a second-stage overheads fraction comprising the third component and a small amount of HFA 125. The second-stage overheads fraction is fed together with impure HFA 125 (containing CFC 115) to the first-stage column or still.

Two-stage embodiments of the process will now be described with reference to the accompanying drawings which show schematic representations of alternative embodiments of the process employing two distillation columns or stills.

BRIEF DESCRIPTION OF THE DRAWINGS

With reference to FIG. 1 of the drawings, impure HFA 125 such as the product of a HFA 125 production process is fed to a distillation column 1 via feed line 2 and a liquid third component (hereinafter HFA 32 for convenience) is fed to column 1 via feed line 3. A bottoms fraction comprising HFA 125 essentially free from CFC 115 is withdrawn via outlet 4 and an overheads fraction comprising HFA 32, CFC 115 and HFA 125 is withdrawn via outlet 5. The overheads fraction is fed to a second distillation column 6. A second-stage overheads fraction comprising HFA 32 and CFC 115 is withdrawn from column 6 via outlet 7 whilst a second-stage bottoms fraction comprising HFA 32 and HFA 125 is withdrawn from column 6 via outlet 8.

The second-stage bottoms fraction withdrawn via outlet 8 may be collected via product line 9 or recycled via recycle line 10 to the first-stage distillation column 1. The second-stage overheads fraction withdrawn via outlet 7 may be passed to disposal or treated to recover HFA 32, in which case the HFA 32 may be recycled to the first-stage distillation column 1 or the second-stage distillation column 2.

Figure 2:
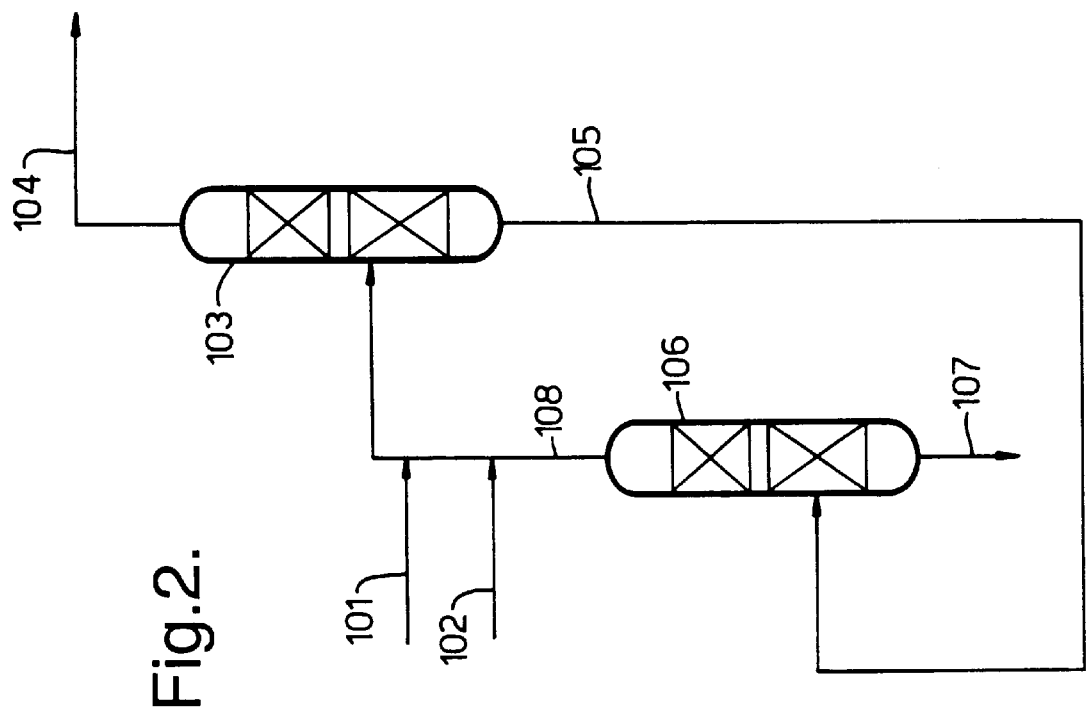
FIG. 2 is a schematic of another embodiment for the purification of pentafluoroethane.
Figure 1:
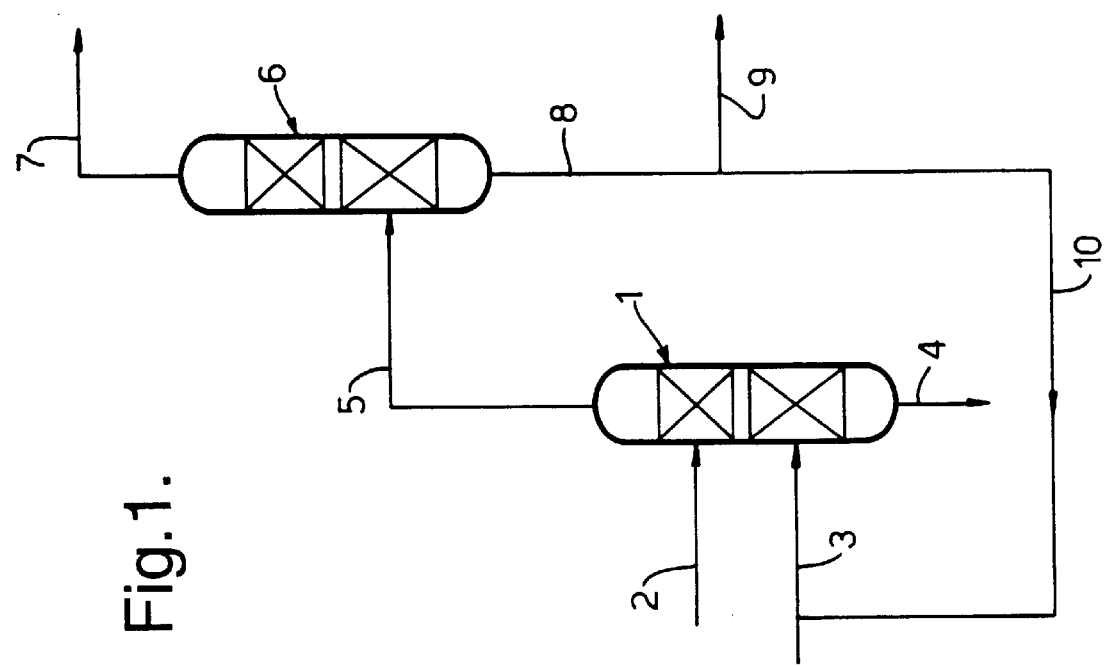
FIG. 1 is a schematic of an embodiment for the purification of pentafluoroethane.

With reference to FIG. 2 of the drawings, impure HFA 125 (containing CFC 115) is fed to a first distillation column 103 via feed line 101 and HFA 32 is fed to the column 103 via feed line 102. The overheads fraction from a second column 106, comprising HFA 32 and HFA 125, is fed via line 108 to the first column 103 and essentially pure HFA 125 is withdrawn as a bottoms fraction via line 107. An overheads fraction comprising HFA 32, CFC 115 and probably a little HFA 125 is withdrawn from the first column 103 via line 104 and a bottoms fraction comprising HFA 32 and HFA 125 is withdrawn via line 105 and fed to the second column 106.

The invention is illustrated but in no way limited by the following examples.

EXAMPLE 1

All compositions are quoted as mole percentages.

A still comprising a 250 ml flask, a 5 stage vacuum jacketed packed column (2.5 cm diameter), condenser and take-off controller was charged at −80° C. with 155.4 g of a mixture of 88.5% HFA 125, 1.6% CFC 115 and 9.9% HFA 32. The column was stabilised under total reflux (still bottom temperature −52° C.) at atmospheric pressure. Following equilibration, a vapour sample was removed from the column top and was shown by GC analysis to have the composition:

HFA 125—80.3% HFA32—16.5% CFC 115—2.6%

Distillation was commenced at a reflux ratio of 5:1 and after approximately half the charge was removed, the distillate composition was:

HFA 125—90.9% HFA32—7.8% CFC 115—0.9%

Comparative Example

The above experiment was repeated using 150 g of a mixture of HFA 125—98.2% and CFC 115—1.8%. After equilibration under total reflux a vapour sample was taken and analysed as:

HFA 125—98.0% CFC 115—2.0%

After distillation of about half the charge at a reflux ratio of 5:1, the distillate composition was:

HFA 125—98.3% CFC 115—1.7%

EXAMPLES 2–4

These examples demonstrate the removal of CFC 115 from impure HFA 125 by selective entrainment in HFA 32 during third-component distillation.

The distillations were performed in a Hastelloy C still equipped with a 3.5 cm internal diameter column having 6 theoretical stages. The still was charged with material, left to equilibrate under total reflux and sampled at 6 points. Column profile compositions were obtained by GC analysis and are recorded as mole percentages.

Comparative Example HFA 125 and CFC 115 distillation with no HFA 32

Charge:
HFA 125=1332 g
CFC 115—26 g
Still Pressure=5.9 Bar
Still Profile

| Sample Position | Temp ° C. | HFA 125 | CFC 115 |
|---|---|---|---|
| Condenser | −5 | 98.72 | 1.28 |
| Top | −2.8 | 98.77 | 1.23 |
| Upper | −3.6 | 98.92 | 1.07 |
| Lower | −3.1 | 99 | 0.99 |
| Bottom | −1.5 | 98.92 | 1.08 |
| Reboiler | 1 | 99.11 | 0.89 |

These results show little change in the relative amounts of 115 and 125 throughout the column.

EXAMPLE 2

HFA 125 CFC 115 Separation with HFA 32.[32:115 Molar Feed Ratio=4.5:1]

Charge:
HFA 125 773 g:
CFC 115 37.6 g:
HFA 32 57 g: 6.6
Still Pressure=6.6 bar

| Sample Position | Temp ° C. | CFC 115 | HFA 32 | HFA 125 |
|---|---|---|---|---|
| Condenser | — | 4.39 | 17.49 | 78.11 |
| Top | −4.5 | 1.35 | 9.76 | 88.87 |
| Upper | −1.4 | 0.33 | 0.9 | 98.76 |
| Lower | −1.2 | 0.33 | 0.58 | 99.08 |
| Bottom | 0 | 0.37 | 0.46 | 99.16 |
| Reboiler | 1.8 | 0.45 | 0.5 | 99.03 |

This example shows that the concentration of CFC 115 alters significantly across the column in the presence of HFA 32, with higher CFC 115 concentrations at the top of the column.

EXAMPLE 3

HFA 125 CFC 115 Separation With HFA 32.[32:115 Molar Feed Ratio=11.1]

Charge
HFA 125=877 g
CFC 115=17 g
HFA 32=168 g
Still Pressure=6.6 Bar

| Sample Position | Temp ° C. | HFA 125 | CFC 115 | HFA 32 |
|---|---|---|---|---|
| Condenser | — | 41.5 | 9.6 | 48.8 |
| Top | −7 | 43.9 | 5 | 51.1 |
| Upper | −5 | 55.6 | 0.9 | 43.5 |
| Lower | −4 | 87.2 | 0.1 | 12.7 |
| Bottom | 2 | — | — | — |
| Reboiler | 3 | 98 | 0.5 | 1.5 |

This example, when compared with Example 2, demonstrates that the concentration of CFC 115 at the top of the still is increased with increasing HFA 32 concentration in the feed.

EXAMPLE 4

HFA 125/CFC 115 Separation With HFA 32.[32:115 Molar Feed Ratio 11:1]

Charge
HFA 125=877 g,
CFC 115=17 g,
HFA 32=168 g:
Still Pressure=12.8 Bar

| Sample Position | Temp ° C. | 125 | 115 | 32 |
|---|---|---|---|---|
| Condenser | 14 | 55.2 | 4.1 | 40.7 |
| Top | 15 | 56.2 | 3.8 | 40 |
| Upper | 17 | 78.3 | 1.4 | 20.2 |
| Lower | 20 | 99.3 | 0.2 | 0.5 |
| Bottom | 23 | 99.3 | 0.2 | 0.5 |
| Reboiler | 43 | 99.2 | 0.2 | 0.7 |

EXAMPLE 5

The use of hydrogen chloride (HCl) as the entrainer in the separation of R125 from R115 in a mixture containing 1 mol % R115 has been modelled using the 'RADFRAC' [Aspen Technology Ltd] calculation package and measured physical properties data which is both publicly and freely available.

The calculations were carried out considering a distillation column with 39 theoretical stages and having a single column feed point at the 14th stage (counting from the top of the column). A 4.67:1.00:0.01 molar ratio of HCl/R125/CFC 115 liquid feed is admitted to a column operating at a pressure of 10 Bara. The column has a total condenser operating at a reflux ratio of 3. A tops fraction of R115/HCl is produced and a bottoms fraction of R125 with minor impurities of R115 and HCl. The R125 product purity achieved is 99.87 mol %.

The column must be controlled such that the HCl composition profile has a significant mole fraction in stages 15–25 where the majority of the R125/R115 separation is to occur. A calculated mass balance for the column is given below in which "lights" is the tops fraction from the column and "product" is the bottoms fraction from the column.

COLUMN MASS BALANCE

| STREAM | TEMP deg C. | MOLAR FLOW HCl | R125 | R115 | MOLE FRACTION HCl | R125 | R115 |
|---|---|---|---|---|---|---|---|
| FEED | −35 | 19.45 | 4.17 | 0.04 | 0.82 | 0.18 | 0 |
| LIGHTS | −31.9 | 19.45 | 0.1 | 0.04 | 0.99 | 0.01 | 0 |
| PRODUCT | 13.2 | 0 | 4.07 | 0.01 | 0 | 1 | 0 |

We claim:

1. A process for the purification of pentafluoroethane by removing chloropentafluoroethane therefrom which comprises adding to the impure pentafluoroethane a halohydrocarbon which undergoes a non-ideal interaction with chloropentafluoroethane and/or with the azeotrope of chloropentafluoroethane and pentafluoroethane such that the volatility of phloropentafluoroethane and/or the azeotrope of chloropentafluoroethane and pentafluoroethane relative to bulk pentafluoroethane is increased and distilling the mixture.

2. A process as claimed in claim 1, in which the halohydrocarbon is polar and has a boiling point below that of HFA 125 whereby its effect in the non-ideal interaction is to increase the volatility of CFC 115 relative to bulk HFA 125, thereby enabling the removal of CFC 115 as a top product from the column or still.

3. A process as claimed in claim 2 in which the top fraction from the distillation column or still comprising chloropentafluoroethane and the halohydrocarbon is then treated to separate halohydrocarbon from CFC 115 and the halohydrocarbon is recycled to the distillation column or still.

4. A process as claimed in claim 2 in which the tops fraction comprising pentafluoroethane, chloropentafluoroethane and the halohydrocarbon is passed to a second distillation column or still from which a top fraction comprising the halohydrocarbon and 115 and a bottom fraction comprising 125 and the halohydrocarbon are recovered.

5. A process as claimed in claim 1 in which the halohydrocarbon has a boiling point less than −50° C. at atmospheric pressure.

6. A process as claimed in claim 1 in which the halohydrocarbon has a boiling point in the range of about −50° C. to −100° C. at atmospheric pressure.

7. A process as claimed in claim 1 in which the halohydrocarbon is a compound of formula $CF_2HX$ in which X is H or Cl.

8. A process as claimed in claim 7 in which the halohydrocarbon is difluoromethane.

9. A process as claimed in claim 1 in which the amount of the halohydrocarbon added is such that the weight ratio of chloropentafluoroethane to halohydrocarbon is in the range from about 10:1 to about 1:10.

10. A process as claimed in claim 1 in which the distillation is effected at a pressure in the range from about 2 bars to about 15 bars.

11. A process as claimed in claim 1 in which the distillation is effected at a temperature such that the distillation occurs under conditions of partial reflux.

12. A process for the purification of pentafluoroethane by removing chloropentafluoroethane therefrom which comprises adding to the impure pentafluoroethane a component having a boiling point less than −50° C. at atmospheric pressure which undergoes a non-ideal interaction with chloropentafluoroethane and/or with the azeotrope of chloropentafluoroethane and pentafluoroethane such that the volatility of chloropentafluoroethane and/or the azeotrope of chloropentafluoroethane and/or the azeotrope of chloropentafluoroethane and pentafluoroethane relative to bulk pentafluoroethane is increased and distilling the mixture.

13. The process according to claim 12 wherein the component is polar and has a boiling point below that of pentafluoroethane whereby its effect in the non-ideal interaction is to increase the volatility of the chloropentafluoroethane relative to the bulk pentafluoroethane, thereby enabling the removal of chloropentafluoroethane as a top product from the distillation column or still, while the pentafluoroethane is collected as a bottom product from the column or still.

14. The process according to claim 13 in which the top product comprises chloropentafluoroethane and the component is subsequently separated therefrom and recycled to the distillation column or still.

15. The process according to claim 13 in which the top product comprises a mixture of pentafluoroethane, chloropentafluoroethane and the component, the mixture is passed to a second distillation column or still, wherein the mixture is further distilled in said second distillation column or still to produce a top fraction comprising the component and chloropentafluoroethane and a bottom fraction comprising pentafluoroethane and the component, and the top and bottom fractions are separately recovered from said distillation column or still.

16. The process according to claim 12 in which the component has a boiling point in the range of about −50° C. to about −100° C. at atmospheric pressure.

17. The process according to claim 12 wherein the component is a hydrogen halide.

18. The process according to claim 17 wherein the hydrogen halide is hydrogen chloride or a mixture of hydrogen chloride with hydrogen fluoride.

19. The process according to claim 18 wherein the hydrogen halide is hydrogen chloride.

20. The process according to claim 12 wherein the component is carbon dioxide.

21. The process according to claim 12 in which the amount of the component aided is such that the weight ratio of chloropentafluoroethane to component is in the range from about 10:1 to about 1:10.

22. The process according to claim 12 in which the mixture is distilled at a pressure ranging from about 2 bars to about 15 bars.

23. The process according to claim 12 in which the mixture is distilled at a temperature such the distillation occurs under condition of partial reflux.

* * * * *